United States Patent [19]

Oh

[11] Patent Number: 4,475,549
[45] Date of Patent: Oct. 9, 1984

[54] ACETABULAR CUP POSITIONER AND METHOD

[76] Inventor: Indong Oh, 851 Lyndon St., South Pasadena, Calif. 91030

[21] Appl. No.: 340,028

[22] Filed: Jan. 18, 1982

[51] Int. Cl.³ ............................................... A61F 5/04
[52] U.S. Cl. .............................. 128/303 R; 128/92 E; 128/92 R
[58] Field of Search ............... 128/303 R, 92 R, 92 E, 128/92 EB, 92 EA

[56] References Cited

U.S. PATENT DOCUMENTS

| | | | |
|---|---|---|---|
| 3,859,992 | 1/1975 | Amstutz | 128/92 E |
| 3,877,433 | 4/1975 | Librach | 128/303 R |
| 3,889,665 | 6/1975 | Ling et al. | 128/92 R |
| 4,305,394 | 12/1981 | Bertuch, Jr. | 128/92 R |

OTHER PUBLICATIONS

DePuy Catalog, 1980, p. A-7.
Zimmer Catalog, 1978, pp. A-12, A-26, A-34.
Richards Orthopedic Catalog, 1978, p. 11.
Richards Spectron TM System Brochure #5384, p. 17.
"Advances in Total Hip Replacement," from *Howmedica Surg. Tech.* by W. H. Harris, Apr. 1980, pp. 18–20.

*Primary Examiner*—C. Fred Rosenbaum
*Assistant Examiner*—C. W. Shedd
*Attorney, Agent, or Firm*—Gordon L. Peterson

[57] ABSTRACT

An acetabular cup positioner for positioning an acetabular cup during hip surgery comprising a head having an axis which is receivable in the acetabular cup, a first arm coupled to the head and extending from the head at an acute angle, and a second arm coupled to the first arm at a location spaced from the head. The second arm extends generally parallel to the axis of the head, and the arms and the axis are in substantially the same plane. First and second handles are coupled to the first arm such that the anteversion angle can be established for the right and left hips by aligning the first and second handles, respectively, with the patient axis.

14 Claims, 5 Drawing Figures

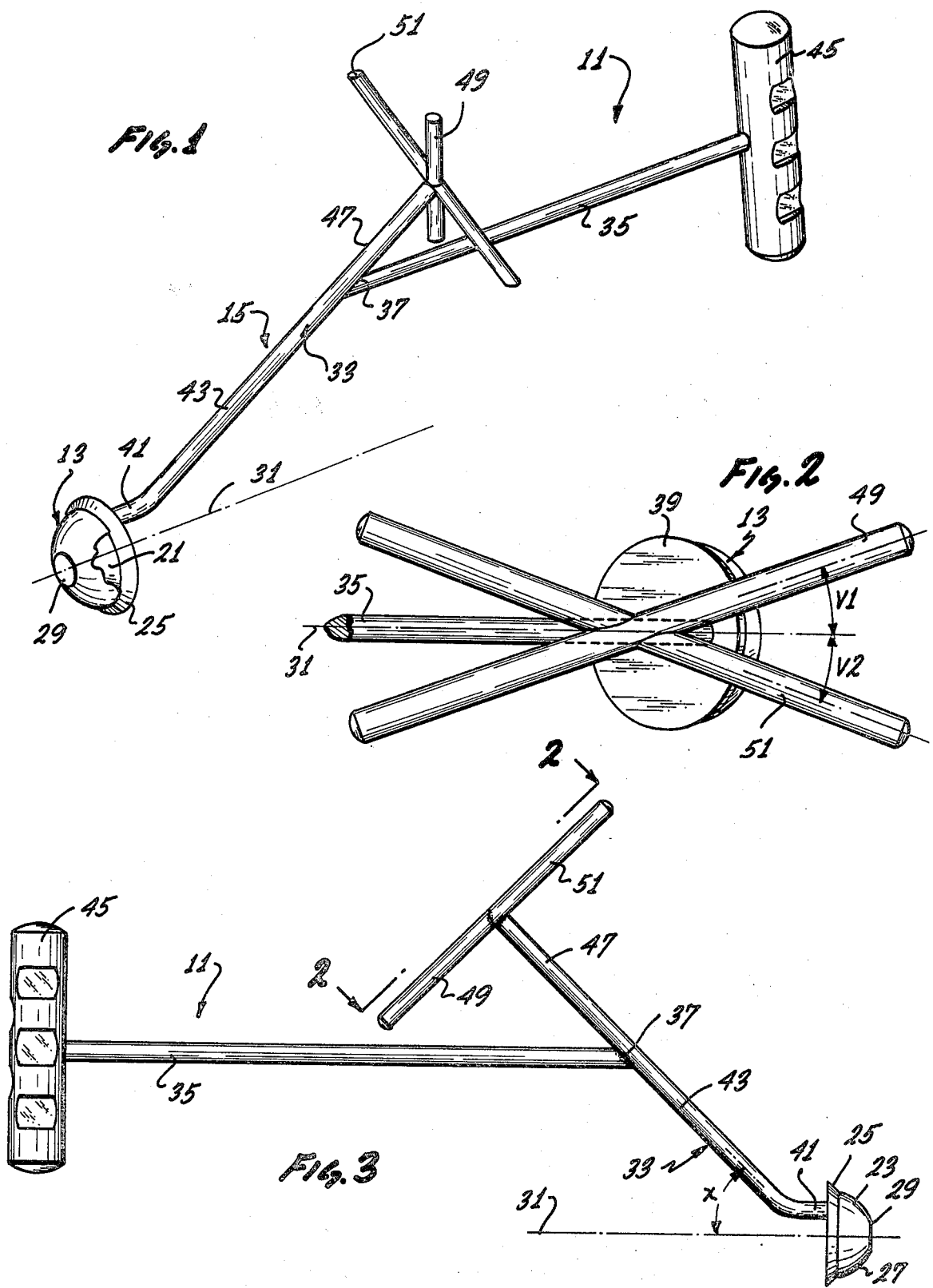

4,475,549

ACETABULAR CUP POSITIONER AND METHOD

BACKGROUND OF THE INVENTION

Deterioration of the hip joint socket or acetabulum requires that an acetabular cup be cemented into the acetabulum to provide the socket for slidably receiving the head. In order to reduce the likelihood of dislocation of the hip, it is very important to accurately position the cup within the acetabulum.

An acetabular cup is positioned by establishing abduction and anteversion angles for the cup. An acetabular cup positioner is used to position the acetabular cup and to hold the cup in position while the cement is hardening. An acetabular cup positioner may include a head which is received within the acetabular cup and one or more arms for moving the head and the acetabular cup. With the head oriented with respect to the acetabular cup, the arm can be moved to position the acetabular cup in the acetabulum. It is known to provide the positioner with an arm that can be rotated to a vertical position to thereby establish the desired abduction angle. The anteversion angle, is obtained utilizing an anteversion guide which measures the anteversion angle from the coronal plane. In other instances, the anteversion angle is established by the surgeon approximating the anteversion angle. In this latter case, the possibility of misorientation and consequent dislocation is increased. The use of a separate anteversion guide unduly complicates the surgical procedures.

SUMMARY OF THE INVENTION

This invention provides an acetabular cup positioner which can be used to establish both the abduction and the anteversion angles. With this invention, the anteversion angle can be quickly and accurately established by aligning a member or other sighting means of the acetabular cup positioner with the axis of the patient. Accordingly, the anteversion guide is eliminated, and the anteversion angle is established much more accurately than is possible with the surgeon estimating the angle.

This invention can advantageously be embodied in an acetabular cup positioner which includes means for engaging the acetabular cup and arm means coupled to the acetabular cup engaging means for moving the acetabular cup in the acetabulum. The arm means includes means for sighting along the axis of the patient to establish the desired anteversion angle.

The acetabular cup positioner of this invention can accommodate a wide range of anteversion angles. Typically, anteversion angles of about 10 to about 25 degrees are utilized. Also, the acetabular cup positioner of this invention enables the abduction angle to be obtained by positioning an arm of the positioner transverse to the patient axis. Thus, both angles can accurately be obtained with the positioner.

Although the sighting means may take different forms, it preferably includes a handle alignable with the patient axis to establish the anteversion angle. When this is done, separate handles are provided for each hip. The handles are appropriately oriented to provide the desired anteversion angle for the right and left hip, respectively, when they are in alignment with the patient axis.

The invention, together with additional features and advantages thereof, may best be understood by reference to the following description taken in connection with the accompanying illustrative drawing.

BRIEF DESCRIPTION OF THE DRAWING

FIG. 1 is a perspective view of an acetabular cup positioner constructed in accordance with the teachings of this invention.

FIG. 2 is an enlarged fragmentary view taken generally along line 2—2 of FIG. 3.

FIG. 3 is a side elevational view of the acetabular cup positioner taken from the back side of FIG. 1.

FIG. 4 is taken from the back of the patient with the patient in a true lateral position, ie., on his side and the head and feet of the patient are to the left and right, respectively.

DESCRIPTION OF THE PREFERRED EMBODIMENT

Figure 4:
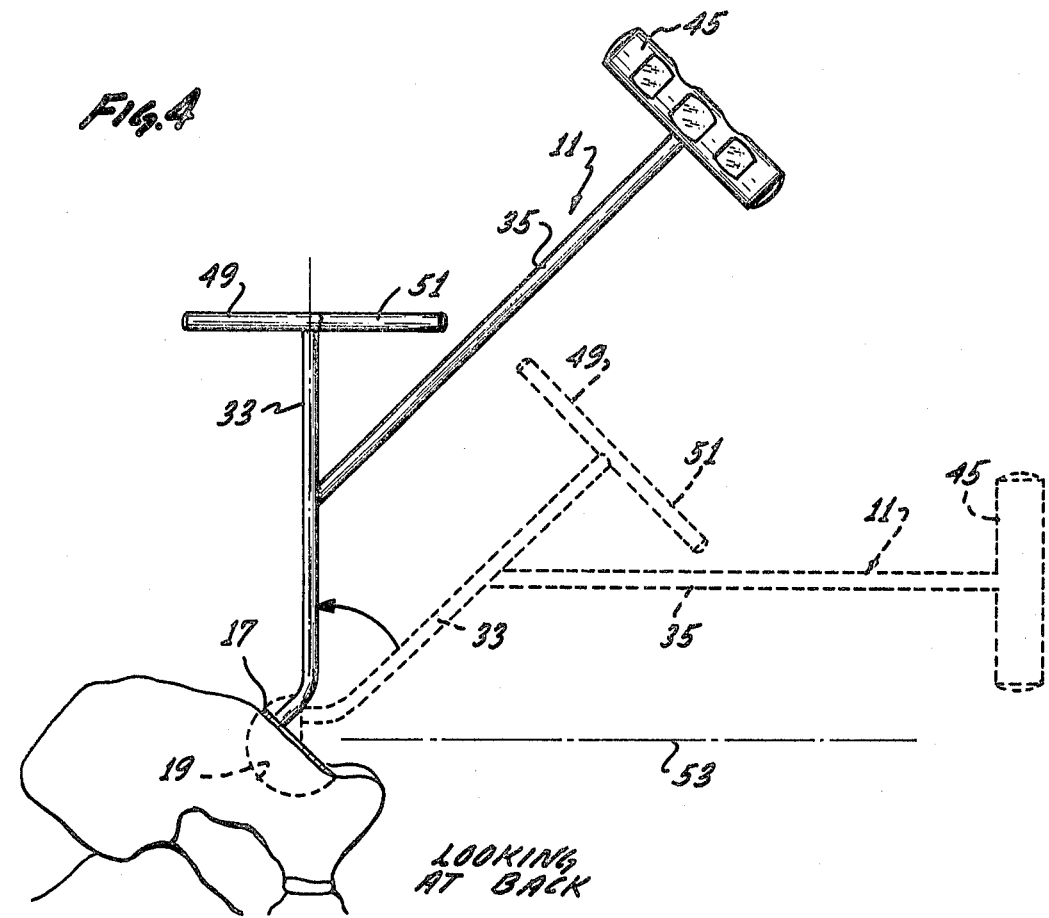
FIG. 4 is an elevational view of the acetabular cup positioner and a portion of the right hip of a patient with the positioner being used to establish the abduction angle. The dashed and solid lines in FIG. 4 show the initial and final positions, respectively.

FIGS. 1–3 show an acetabular cup positioner 11 which generally includes a head 13 and arm means 15 coupled to the head to facilitate manual movement of the head. The head 13 can be of virtually any construction that will enable the head to engage and move an acetabular cup 17 (FIG. 4) in the acetabulm 19. In the embodiment illustrated, the head comprises a plug 21 of suitable metal or other material, and a cover 23 of a material, such as silicone, which is compressible and has a relatively high coefficient of friction. The plug 21 has an annular flange or disc 25 which is integral with the plug 21. The cover 23 terminates at the flange 25.

The cover 23 has a generally hemispherical outer surface 27, except for a cylindrical opening 29. Thus, the cover 23 is adapted to be received within the acetabular cup 17, and the disc 25 is adapted to engage the rim of the acetabular cup.

The head 13 has an axis 31 which extends radially through the center of the hemispherical head and is perpendicular to the opening 29. The arm means 15 includes a first arm 33 coupled to the head 13 and a second arm 35 coupled to the arm 33 at a location 37 spaced from the head. In the embodiment illustrated, the head 13 has a back surface 39 which is planar, and the arm is joined to the surface 39 as by soldering at a location displaced from the axis 31 and adjacent the periphery of the flange 25.

The arm 33 has a parallel leg 41 parallel to, and spaced from, the axis 31 and perpendicular to the surface 39 and an inclined leg 43 forming an acute angle X (FIG. 3) with the axis 31. Spacing the arm 33 from the axis 31 provides easier access to the inferior corner of the acetabular rim for removing excess cement. As explained more fully hereinbelow, the complement of the angle X, i.e., 90°-X, is the abduction angle which the acetabular cup positioner 11 is adapted to establish. Although the cup positioner may be adapted to establish any desired abduction angle, the common range of abduction angles is 35 to 45 degrees, and thus, the angle X is typically in the range of 45 to 55 degrees. In the embodiment illustrated, the angle X is 45 degrees.

The arm 33 and 35 can advantageously take the form of elongated rods of generally circular or square crosssectional configuration. The arms 33 and 35 are preferably constructed of a metal and may be welded together at the location 37 to avoid contact with adjacent soft tissue of the patient. The arm 35 terminates outwardly in a handle 45.

The arms 33 and 35 intersect to define a plane, and this plane contains the axis 31. Although different constructions are possible, in the embodiment illustrated, the arm 35 is parallel to the axis 31 and thus forms a 45-degree angle with a portion 47 of the inclined leg 43 which projects beyond the location 37.

Handles 49 and 51 are attached to the outer end of the arm 33. The handles 49 and 51 extend transversely to the arm 33, and in the embodiment illustrated, are perpendicular to the arm 33. The handles 49 and 51 form angles V1 and V2, respectively, with the plane defined by the arms 33 and 35 as viewed in FIG. 2, i.e., as viewed in a reference plane which is perpendicular to the plane of the arms 33 and 35 and in which the axis 31 appears as a line or as viewed normal to the arm 33 (FIG. 2). As shown in FIG. 2, the angles V1 and V2 are measured between the plane defined by the arms 33 and the central axes of the handles 49 and 51, respectively. As viewed in FIG. 2, the handles 49 and 51 cross to form an X, with the plane formed by the arms 33 and 35 bisecting the X.

Each of the angles V1 and V2 is equal to the desired anteversion angle. The angles V1 and V2 may be equal or different and are typically in the range of from about 10 degrees to about 25 degrees, although angles of different magnitudes may be employed if desired. Accordingly, the acute angle defined by the handles 49 and 51, i.e., V1 plus V2, may typically be in the range of from about 20° to about 50°. In the illustrated embodiment, the angles V1 and V2 are each 20°.

The axes of the handles 49 and 51 define sighting means that can be used for establishing the correct anteversion angle for the left and right hips, respectively. In addition, the handles 49 and 51 serve as handles to facilitate manipulation of the cup positioner 11 by the surgeon.

In use of the acetabular cup positioner 11, the head 13 is inserted into the acetabular cup 17 before the acetabular cup is inserted into the acetabulum. The head 13 is inserted into the acetabular cup 17 until the disc 25 bears against the rim of the cup 17 to thereby assure that the head is fully seated in the cup. This automatically orients the acetabular cup 17 relative to the cup positioner 11 in two planes, and if the cup 17 is symmetrical, this automatically orients the cup relative to the cup positioner in all three planes. However, if the acetabular cup 17 is not symmetrical, the surgeon should rotate the cup on the cup positioner 11 to orient the acetabular cup 17 about the axis 31. Generally, the axis of the acetabular cup 17 will coincide with the axis of the head 13.

With the acetabular cup 17 properly oriented on the acetabular cup positioner 11 and the acetabular cup in the acetabulum, the positioner 11 is then rotated to bring the plane of the arms 33 and 35 in line with the patient axis 53, and this is the position of the acetabular cup positioner 11 in FIG. 4. To obtain the desired abduction angle, the acetabular cup positioner 11 is first placed in the dashed-line position shown in FIG. 4 in which the second arm is paralled to the patient axis 53. The positioner 11 is then rotated counterclockwise in a vertical plane as viewed in FIG. 4 to the solid-line position in which the arm 33 is perpendicular to the patient axis 53. This establishes the correct abduction angle which, in the embodiment illustrated, is 45 degrees.

Figure 5:
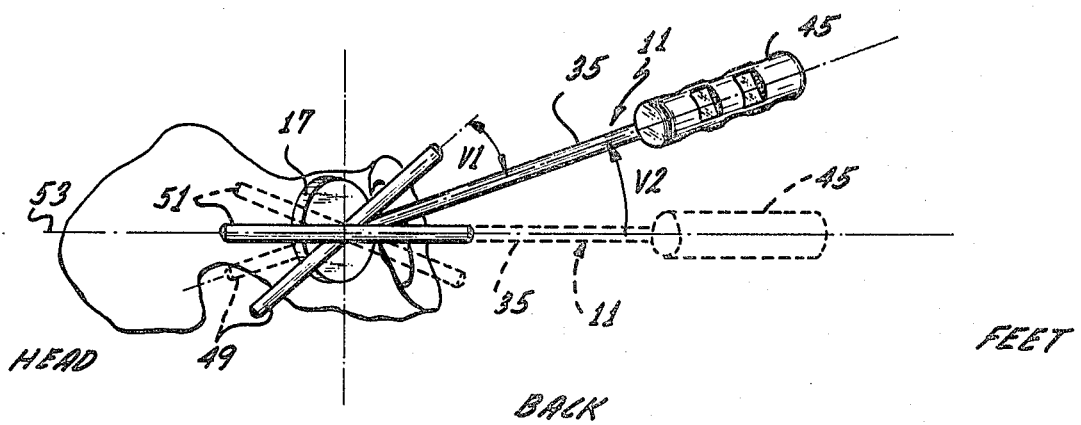
FIG. 5 is a top plan view illustrating how the cup positioner is used to establish the anteversion angle for the right hip with the dashed and solid lines showing the initial and final positions, respectively, of the positioner. The patient is in the same position as in FIG. 4.

The dashed-line position of the positioner 11 in FIG. 5 corresponds to the full-line position of the positioner 11 in FIG. 4. To establish a desired anteversion angle, the surgeon simply rotates the cup positioner 11 counterclockwise as viewed in FIG. 5 through the angle V2 to bring the handle 51 into alignment with the patient axis 53. The surgeon can sight along the handle 51 to assure that correct alignment is established. No anteversion guide or other device is necessary to correctly establish the anteversion angle. To remove the positioner 11 from the cup 17 without moving the cup, the surgeon inserts a rigid blunt rod (not shown) through the opening 29 and against the cup 17.

In the examples shown in FIGS. 4 and 5, the surgery is being performed on the right hip. The positioner 11 can be used in the same manner on the left hip, except that the handle 49 is brought into alignment with the patient axis 53 to establish the correct anteversion angle. Thus, the same positioner 11 is usable for both the left and right hips to establish both the abduction and anteversion angles.

Although the handles 49 and 51 are the preferred means for enabling the surgeon to sight along the patient axis 53 to obtain the desired anteversion angle, other means to accomplish this purpose could be used. For example, one or both of the handles could be replaced with different members having lines of sight thereon corresponding to the axes of the handles. Of course, the head 13 can be of different sizes to accommodate acetabular cups of different internal diameters.

Although an examplary embodiment of the invention has been shown and described, many changes, modifications and substitutions may be made by one having ordinary skill in the art without necessarily departing from the spirit and scope of this invention.

I claim:

1. An acetabular cup positioner for positioning an acetabular cup during hip surgery on a patient to establish abduction and anteversion angles of the acetabular cup in the acetabulum, said acetabular cup positioner comprising:
   acetabular cup engaging means for engaging the acetabular cup and moving the acetabular cup in the acetabulum to provide the desired abduction and anteversion angles of the acetabular cup;
   arm means coupled to the acetabular cup engaging means and manually movable to move the acetabular cup engaging means to position the acetabular cup in the acetabulum; and
   said arm means including means for sighting along the axis of the patient to establish the anteversion angle.

2. An acetabular cup positioner as defined in claim 1 wherein said sighting means establishes an anteversion angle for the acetabular cup of from about 10 degrees to about 25 degrees when said sighting means is sighted along the patient axis.

3. An acetabular cup positioner as defined in claim 1 wherein said sighting means is a first sighting means and establishes the anteversion angle for the right hip and said arm means includes second means for sighting along the axis of the patient to establish the anteversion angle for the left hip.

4. An acetabular cup positioner as defined in claim 1 wherein said sighting means includes a handle alignable with the patient axis to establish an anteversion angle of from about 10 degrees to about 25 degrees.

5. An acetabular cup positioner as defined in claim 1 wherein said arm means includes means for sighting relative to the patient to establish an abduction angle for the acetabular cup.

6. An acetabular cup positioner as defined in claim 1 wherein said arm means includes a first arm extending from the acetabular cup engaging means at an angle such that when the first arm extends transverse to the patient axis, the acetabular cup has an abduction angle of from about 35 degrees to about 45 degrees and said sighting means includes a handle coupled to the first arm at an angle such that with the handle extending generally parallel to the patient axis, the acetabular cup has an anteversion angle of from about 10 degrees to about 25 degrees.

7. An acetabular cup positioner as defined in claim 1 wherein said acetabular cup engaging means has an opening through which a member can be inserted to at least assist in removing the cup positioner from the acetabular cup.

8. An acetabular cup positioner for positioning an acetabular cup comprising:
  a head at least partially receivable in the acetabular cup which is to be positioned, said head having an axis;
  a first arm coupled to the head, at least a portion of the first arm extending from the head at an acute angle to the axis;
  a second arm coupled to the first arm at a location spaced from the head, said first and second arms and the axis of the head being substantially in a first plane; and
  a handle coupled to the first arm and extending generally transversely to the first arm, said handle forming an acute angle with said first plane of from about 10 degrees to about 25 degrees as viewed in a reference plane which is perpendicular to said first plane and in which said axis appears as a line.

9. An acetabular cup positioner as defined in claim 8 wherein said handle is a first handle and said acetabular cup positioner includes a second handle coupled to said first arm and extending generally transverse to the first arm, said second handle forming an angle as viewed from said reference plane with said first handle of from about 20 degrees to about 50 degrees with said first plane substantially bisecting said last-mentioned angle.

10. An acetabular cup positioner as defined in claim 9 wherein a portion of said first arm extends beyond said first location whereby said location is intermediate said portions of said first arm and said handles are mounted on the portion of the first arm which extends beyond said location.

11. An acetabular cup as defined in claim 10 wherein said angles formed by the first and second handles are equal, said head has an opening through which a member can be inserted to at least assist in removing the head from the acetabular cup and said first arm has an axis which is spaced from the axis of the head.

12. An acetabular cup positioner as defined in claim 8 wherein said first arm has an axis which is spaced from the axis of the head.

13. A method of positioning an acetabular cup in the acetabulum of a patient during surgery utilizing an acetabular cup positioner which includes an acetabular cup engaging member, an arm coupled to the acetabular cup engaging member and sighting means on the arm and wherein the acetabular cup engaging member engages the acetabular cup and the acetabular cup is seated within the acetabulum, said method comprising:
  manually moving the arm means to establish the desired abduction angle; and
  aligning the sighting means with the patient axis to establish the anteversion angle.

14. A method as defined in claim 13 wherein the arm includes second sighting means and said method includes manually moving said arm to place said second sighting means generally transverse to the patient axis to establish the abduction angle.

* * * * *